US010617360B2

(12) United States Patent
Jeon et al.

(10) Patent No.: US 10,617,360 B2
(45) Date of Patent: Apr. 14, 2020

(54) WRIST-WORN APPARATUS FOR DETECTING BIO-SIGNAL

(71) Applicants: Hyundai Motor Company, Seoul (KR); LG Innotek Co., LTd., Seoul (KR)

(72) Inventors: Seul Ki Jeon, Gyeonggi-do (KR); Nam Woong Hur, Gyeonggi-do (KR); Eung Hwan Kim, Seoul (KR); Jin Ho Gwon, Seoul (KR); Sang Hun Lee, Seoul (KR)

(73) Assignees: Hyundai Motor Company, Seoul (KR); LG Innotek Co., LTd., Seoul (KR)

( * ) Notice: Subject to any disclaimer, the term of this patent is extended or adjusted under 35 U.S.C. 154(b) by 387 days.

(21) Appl. No.: 15/250,374

(22) Filed: Aug. 29, 2016

(65) Prior Publication Data

US 2017/0188953 A1     Jul. 6, 2017

(30) Foreign Application Priority Data

Jan. 4, 2016   (KR) ........................ 10-2016-0000361

(51) Int. Cl.
*A61B 5/1455*      (2006.01)
*A61B 5/00*        (2006.01)
*A61B 5/024*       (2006.01)

(52) U.S. Cl.
CPC ........ *A61B 5/6824* (2013.01); *A61B 5/02433* (2013.01); *A61B 5/02438* (2013.01); *A61B 5/1455* (2013.01); *A61B 5/6831* (2013.01); *A61B 2562/0238* (2013.01); *A61B 2562/043* (2013.01); *A61B 2562/185* (2013.01)

(58) Field of Classification Search
None
See application file for complete search history.

(56) References Cited

U.S. PATENT DOCUMENTS

| 6,223,063 | B1* | 4/2001 | Chaiken | ............ | A61B 5/02427 600/310 |
| 2013/0189641 | A1* | 7/2013 | Perfect | ............... | A61B 1/00089 433/29 |
| 2014/0051955 | A1* | 2/2014 | Tiao | ................... | A61B 5/14552 600/323 |

(Continued)

FOREIGN PATENT DOCUMENTS

| JP | 2001-061796 A | 3/2001 |
| JP | 2002-360530 A | 12/2002 |

(Continued)

*Primary Examiner* — Eric F Winakur
*Assistant Examiner* — Marjan Fardanesh
(74) *Attorney, Agent, or Firm* — Mintz Levin Cohn Ferris Glovsky and Popeo, P.C.; Peter F. Corless (57) ABSTRACT

An apparatus for measuring a bio-signal includes: a light source emitting a predetermined amount of light into a human body; a light receiving unit receiving at least some of the predetermined amount of light; and a cover, which is touchable by the human body, protecting the light source and the light receiving unit. The light source and the cover are arranged such that the light source and the cover are separated by a first gap, the light receiving unit and the cover are arranged such that the light receiving unit and the cover are separated by a second gap, and the first gap is less than the second gap.

18 Claims, 8 Drawing Sheets

(56) References Cited

U.S. PATENT DOCUMENTS

2014/0200423 A1* 7/2014 Eisen ................. A61B 5/14551
                                                                600/340
2014/0371601 A1* 12/2014 Fei ..................... A61B 5/02427
                                                                600/476
2015/0025393 A1   1/2015 Hong et al.

FOREIGN PATENT DOCUMENTS

| JP | 2006-296564 A | 11/2006 |
| KR | 2011-0111827 A | 10/2011 |
| KR | 2015-0107944 A | 9/2015 |

* cited by examiner

WRIST-WORN APPARATUS FOR DETECTING BIO-SIGNAL

CROSS-REFERENCE TO RELATED APPLICATION

This application claims priority to and the benefit of Korean Patent Application No. 10-2016-0000361, filed on Jan. 4, 2016 in the Korean Intellectual Property Office, the disclosure of which is hereby incorporated by reference as if fully set forth herein.

TECHNICAL FIELD

The disclosure relates generally to a wrist-worn apparatus for detecting a bio-signal, and more particularly, to an apparatus and a method for enhancing a quality of bio-signal based on placement of light-emitting and receiving devices configured to detect a bio-signal and structural design optimization of optics devices.

BACKGROUND

Recently, advances in technology for monitoring a physical condition in real-time have been made. To this end, a bio-signal can be used for checking a physical condition in real-time. A bio-signal measurement can be achieved by an interface for handling bio-signals and a technique for monitoring the bio-signals. For example, the interface for handling the bio-signals may generate a command or an instruction for detecting bio-signals or operating a medical device in response to the bio-signals. The technique for monitoring the bio-signals allows for recognizing distinct features of the bio-signals in order to, for example, determine bodily diseases or diagnose a mental illness.

There are various measurable bio-signals such as an Electroencephalography (EEG), an Electrocardiography (ECG), an Electromyography (EMG), a Photoplethysmography (PPG), an Electrooculography (EOG), breathing, and the like. Among them, the PPG is one of the more easily monitored bio-signals in real-time.

A PPG signal, which is detected based on optical characteristics of a measuring device, shows a heart rate synchronized with cardiac impulses. A pressure generated by cardiac impulses makes blood flow through blood vessels. The generated pressure may affect the bloodstream at capillaries in fingers, toes, earlobes, or the like. Arterial blood flowing through capillaries in the distal of body can be supplied into cellular tissues, while returning into the heart via veins. Accordingly, whenever cardiac impulses occurs, a blood flow rate of the arterial blood flowing through capillaries in the distal of body is changed, i.e., increased or decreased.

Meanwhile, when a light source of a PPG measuring sensor emits a light into a part of body, some of the light is absorbed into blood, bone, and/or tissue while the other of the light is penetrated or reflected so as to enter into a light receiving device. Absorbed light subtracted from an original emitted light can equal a penetrated light or a reflected light recognized by the light receiving device. The change of the penetrated or reflected light may show a blood flow change. Thus, the PPG measuring sensor uses the light receiving device to detect an amount of light so that the blood flow change synchronized with the cardiac impulses can be measured.

An apparatus for measuring the PPG signal may be implemented relatively simply and can readily recognize a user's movement. However, since the PPG signal can be distorted by noises caused by the user's movement, the apparatus should remove recognized noises while handling the PPG signal. In order to effectively process the noises, a wrist-worn device can be used.

SUMMARY

In a device wearable at a wrist of a user, an apparatus and a method for arranging light-emitting and receiving devices can enhance a performance of the device which is capable of measuring a Photoplethysmography (PPG) signal. Optimized structure and design of a wearable device can improve a quality of the PPG signal and enhance an accuracy of PPG signal measurements.

Further, even though the PPG signal is measurable at the wrist with about 1/10 to 1/20 of the signal strength of one measurable at a fingertip, an apparatus and a method for arranging light-emitting and receiving devices can detect a bio-signal, such oxygen saturation in blood, which may be difficult to measure of recognize because of a low signal quality.

Even further, an apparatus for measuring a bio-signal can have a structure and an arrangement of components which corresponds with the structure of a human body which wears the apparatus.

According to embodiments of the present disclosure, an apparatus for measuring a bio-signal includes: a light source emitting a predetermined amount of light into a human body; a light receiving unit receiving at least some of the predetermined amount of light; and a cover, which is touchable by the human body, protecting the light source and the light receiving unit. The light source and the cover are arranged such that the light source and the cover are separated by a first gap, the light receiving unit and the cover are arranged such that the light receiving unit and the cover are separated by a second gap, and the first gap is less than the second gap.

The light source and the light receiving unit can be arranged with a separation distance between them of about 5 to about 6 mm.

The light source can emit at least one of an infrared ray and a visible ray.

An amount of light can be reflected by a portion of the human body and can enter into the light receiving unit, the portion of the human body is a wrist, and both of the light source and the light receiving unit can be located over a radial in the wrist.

Locations of the light source and the light receiving unit can differ based upon whether the apparatus is left-handed or right-handed.

The first gap between the light source and the cover can be less than about 1 mm, while the second gap between the light receiving unit and the cover can be less than about 2 mm.

The apparatus can further include a light barrier formed between the light source and the light receiving unit.

The light barrier can extend into the cover so that a portion of the cover covering the light source is separate from a portion of the cover covering the light receiving unit.

The apparatus can further include a lens disposed over the light receiving unit.

The lens can be a concave lens having a convex surface.

The apparatus can detect a photoplethysmography (PPG) signal based on a change of an amount of light received at the light receiving unit.

Furthermore, in accordance with embodiments of the present disclosure, a PPG sensor includes: a light-emitting diode and a photo diode formed over a support layer; an isolating barrier formed between the light-emitting diode and the photo diode; and a cover protecting the light-emitting diode and the photo diode. The light-emitting diode and the cover are arranged such that the light-emitting diode and the cover are separated by a first gap, the photo diode and the cover are arranged such that the photo diode and the cover are separated by a second gap, and the first gap is less than the second gap.

The light-emitting diode can emit at least one of an infrared ray and a visible ray.

The light-emitting diode and the photo diode can be arranged with a separation distance between them of about 5 to about 6 mm.

The light-emitting diode can include a plurality of light-emitting diodes, each located adjacent to one another.

The locations of the light-emitting diode and the photo diode may differ according to a part of a human body on which the PPG sensor is worn.

Both of the light-emitting diode and the photo diode can be located over a radial in a wrist.

The first gap can be less than about 1 mm, while the second gap can be less than about 2 mm.

The isolating barrier can extend into the cover so that a portion of the cover covering the light-emitting diode is separate from a portion of the cover covering the photo diode.

The PPG sensor can further include a blocking layer surrounding a portion of the cover positioned over the photo diode, the portion of the cover being formed in a convex shape.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure. In the drawings.

DETAILED DESCRIPTION OF THE EMBODIMENTS

Reference will now be made in detail to the embodiments of the disclosure, examples of which are illustrated in the accompanying drawings. In the drawings, the same elements are denoted by the same reference numerals, and a repeated explanation thereof will not be given. The suffixes "module" and "unit" of elements herein are used for convenience of description and thus can be used interchangeably and do not have any distinguishable meanings or functions.

The terms "a" or "an", as used herein, are defined as one or more than one. The term "another", as used herein, is defined as at least a second or more. The terms "including" and/or "having" as used herein, are defined as comprising (i.e., open transition). The term "coupled" or "operatively coupled" as used herein, is defined as connected, although not necessarily directly, and not necessarily mechanically.

In the description of the disclosure, certain detailed explanations of related art are omitted when it is deemed that they may unnecessarily obscure the essence of the disclosure. The features of the disclosure will be more clearly understood from the accompanying drawings and should not be limited by the accompanying drawings. It is to be appreciated that all changes, equivalents, and substitutes that do not depart from the spirit and technical scope of the disclosure are encompassed in the disclosure.

Figure 1:
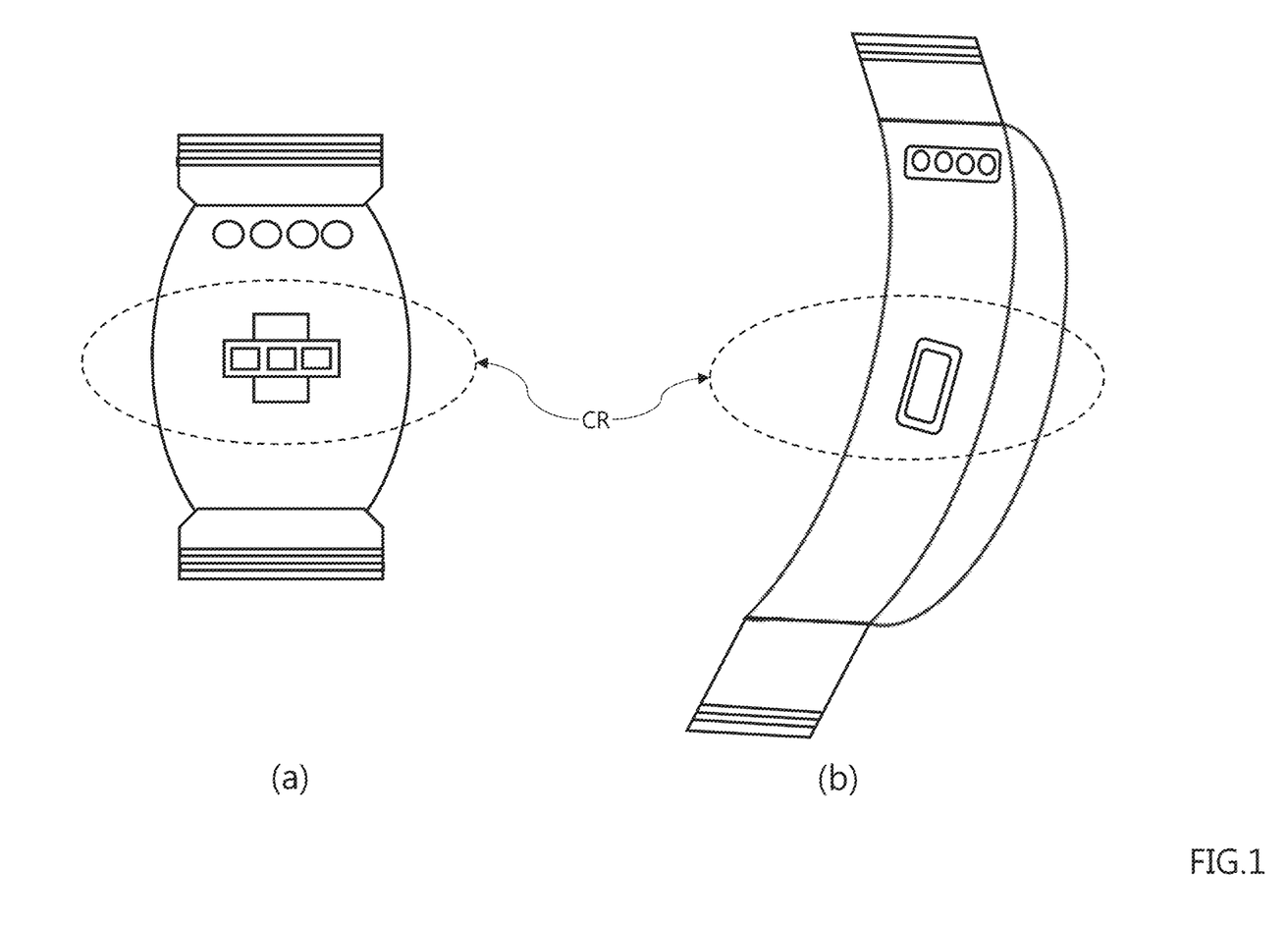
FIG. 1 shows a conventional wrist wearable device.

Preliminarily, FIG. 1 shows a conventional wrist wearable device and its drawback. Particularly, (a) and (b) of FIG. 1 describes an example of a smart watch wearable at a wrist, which includes a sensor for measuring a bio-signal.

As shown in (a) and (b) of FIG. 1, in order to reduce current consumption, a light-emitting device and a light receiving device are arranged adjacent to each other inside a Photoplethysmography (PPG) sensor included in the wrist wearable device. The light-emitting device and the light receiving device are located in a center (CR) of the wrist wearable device described in (a) and (b) of FIG. 1. When a user wears the device at his or her wrist, the center (CR) of the wrist wearable device mostly places on a center of his or her wrist. Since a Photoplethysmography (PPG) signal measurable at a wrist may have about $1/10$ to $1/20$ signal strength of one measurable at a fingertip, a PPG signal measured through the wearable device having the light-emitting device and the light receiving device located in the center (CR) may not be sufficient for a signal analysis. For example, it is challenging when the PPG signal is used for recognizing oxygen saturation or the like in blood, which requires a more accurate signal analysis than checking cardiac impulses.

To overcome the above-described issues, it is necessary to optimize arrangements of the light-emitting device and the light receiving device for detecting a bio-signal in a wrist wearable device, and to improve a design and a structure of optical devices. In a wearable device, optimized arrangement of components and/or improved design and structure of the components can improve a quality of signal regarding the bio-signal and enhance an accuracy of detecting the bio-signal. In order to enhance a performance of a bio-signal measuring apparatus wearable at a particular part of human body, there are several ways such as adjusting a separation distance between light-emitting and receiving devices, adjusting a light pass/route from the light-emitting device to the light receiving device so that the light pass/route can correspond to a vascularity of the particular part of human body, adjusting a gap between the light-emitting and receiving devices and a human body (e.g., skin), improving a structure of a light barrier between the light-emitting and receiving devices so as to isolate a light and reduce a leakage of light, and applying a structure of lens to the light receiving device in order for enhancing an efficiency of receiving a light. Through one or more of the means described above, the bio-signal measuring apparatus can improve a quality of signal, and enhance an accuracy of detecting the bio-signal.

Figure 2:
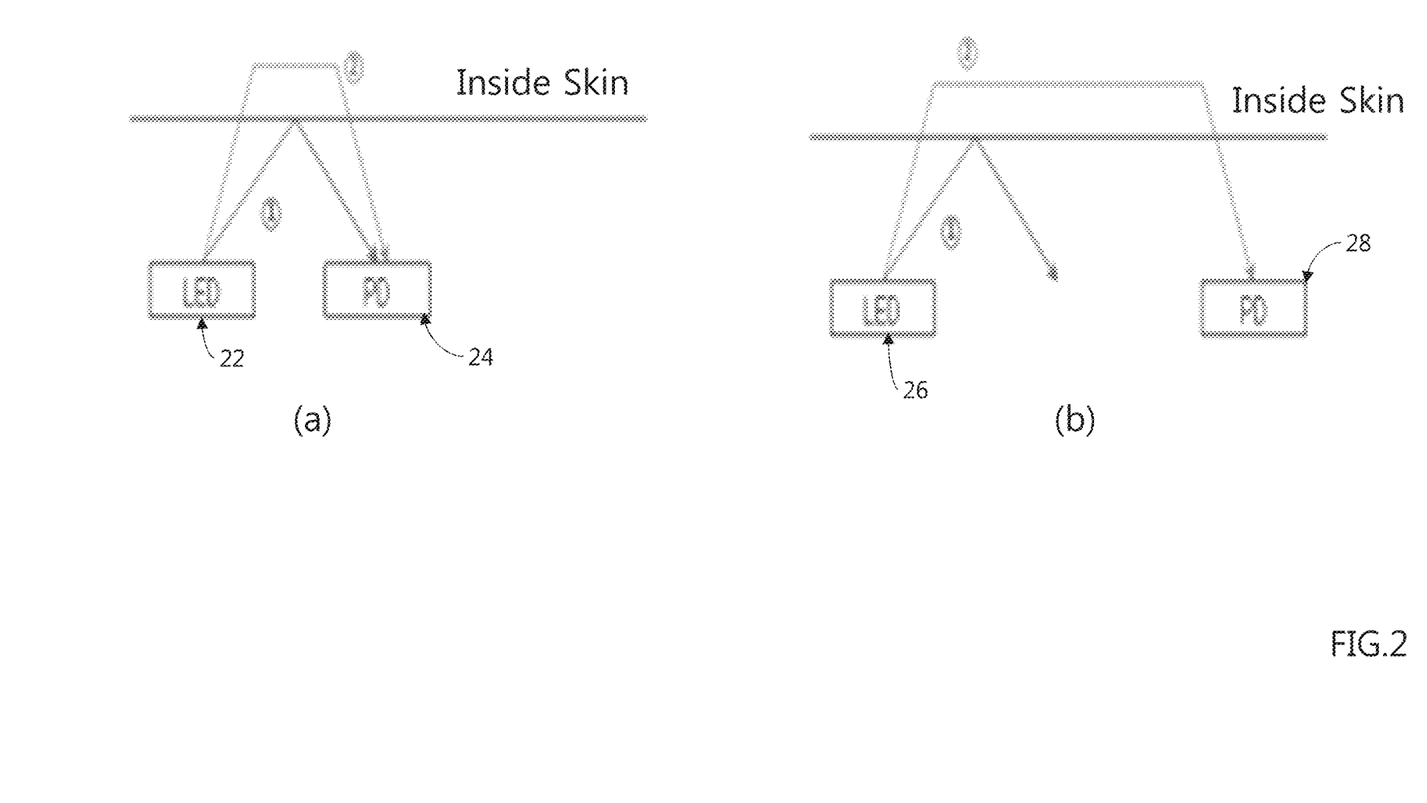
FIG. 2 shows a first structure of an apparatus for measuring a bio-signal according to embodiments of the present disclosure.

Referring now to the presently disclosed embodiments, FIG. 2 shows a first structure of an apparatus for measuring a bio-signal according to embodiments of the present disclosure.

As shown in FIG. 2, the apparatus for measuring a bio-signal can include a light source 22, 26 configured to emit a predetermined amount of light into a human body and a light receiving device 24, 28 configured to receive some of the predetermined amount of light emitted from the light source 22, 26. Particularly, while (a) shows a case when a distance between the light source 22 and the light receiving device 24 is short, (b) shows a case when a distance between the light source 26 and the light receiving device 28 is larger than a predetermined distance.

Referring to (a) of FIG. 2, since a signal strength of signals received by the light receiving device 24 becomes stronger as a separation distance between the light source 22 and the light receiving device 24 becomes closer, the light receiving device 24 can be adjacent to the light source 22 so as to reduce a power consumption. For example, the separation distance between the light source 22 and the light receiving device 24 can be less than or equal to about 2 mm. Herein, there are two types of rays which is received by the light receiving device 24 after emitted by the light source 22 (i.e., a first ray entered into the light receiving device 24 after reflected by a skin, and a second ray entered into the receiving device 24 after reflected by an inner part under the skin). The first ray (1) can be generated since refractive indices of an atmosphere and human's skin are different. Unlike the second ray (2) delivered through an inner human body, the first ray (1) entered after reflected by the skin can be considered a sort of noises which do not contribute towards measuring a bio-signal.

Referring to (b) of FIG. 2, in order to avoid that the light receiving device 28 receives a noise such as a first ray (1), the light receiving device 28 and the light source 26 are arranged with a separation distance of about 5 to 6 mm. Herein, if a separation distance between the light receiving device 28 and the light source 26 is adjusted, the first ray (1) delivered after reflected by a skin may not be entered into the light receiving device 28. In this case, a quality of signal regarding a second ray (2) delivered after reflected or refracted by an inner part of a human body can be enhanced.

Figure 3:
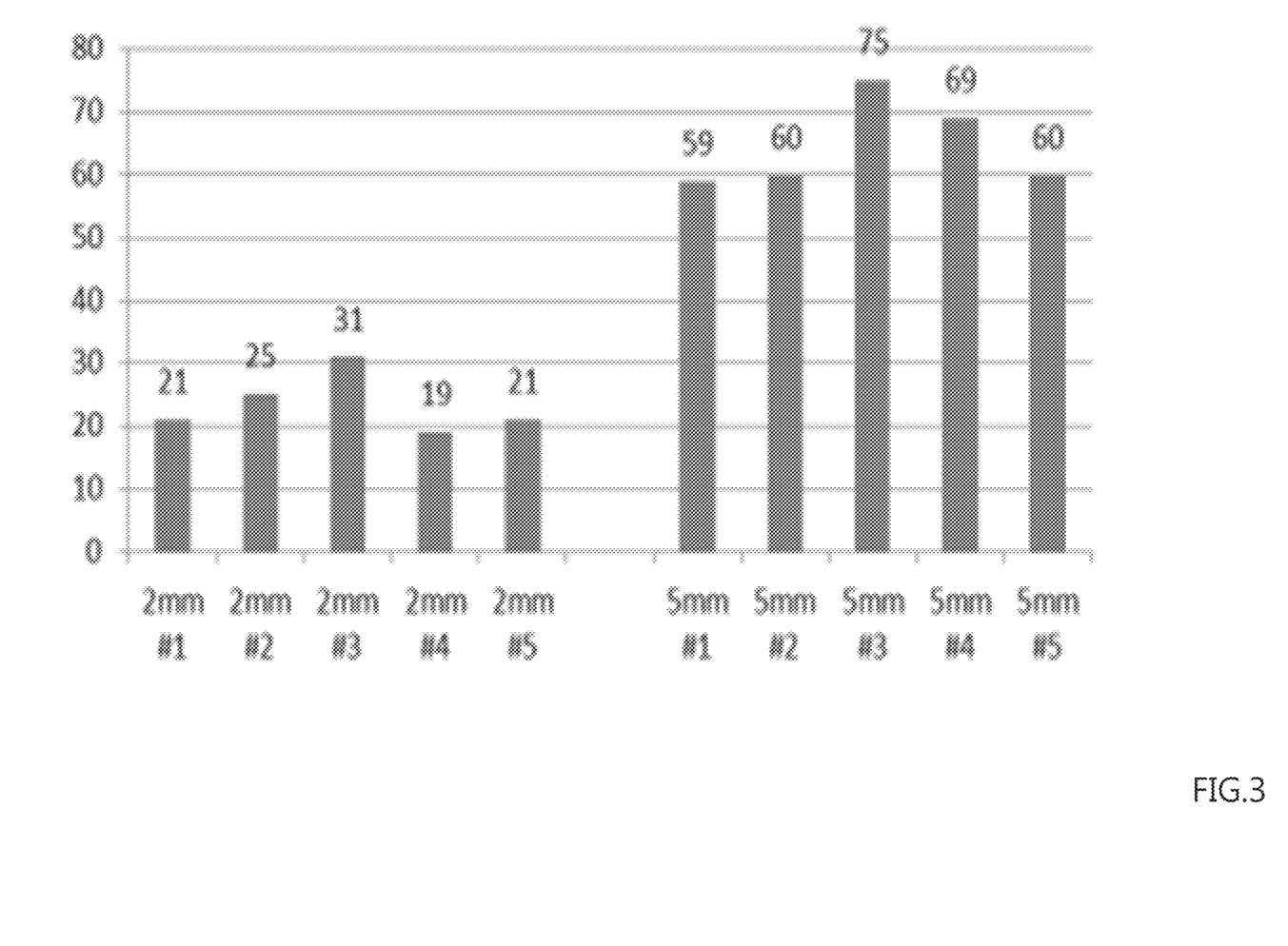
FIG. 3 describes an effect that can come from the first structure shown in FIG. 2.

FIG. 3 describes an effect that can come from the first structure shown in FIG. 2.

As shown in FIG. 3, in two cases when a separation distance between a light receiving device and a light source, emitting a red-colored ray and/or an infrared ray used for recognizing oxygen saturation, is 2 mm and 5 mm, qualities of signals can be compared with each other. FIG. 3 shows that the quality of signals in the case when the separation distance between the light receiving device and the light source is 5 mm is better than one in the case when the separation distance is 2 mm.

As described above, in a bio-signal sensor, when a separation distance between a light receiving device and a light source is sufficient to avoid receiving a ray reflected by a skin, a quality of signals can be improved. However, a strength of valid signals received by the light receiving device can be weak, too. Further, even because of user's skin color or user's vascularity in a particular body where the bio-signal sensor is worn, an optimized separation distance between the light receiving device and the light source can be different. Thus, more factors could be considered to get the optimized separation distance between the light receiving device and the light source.

Figure 4:
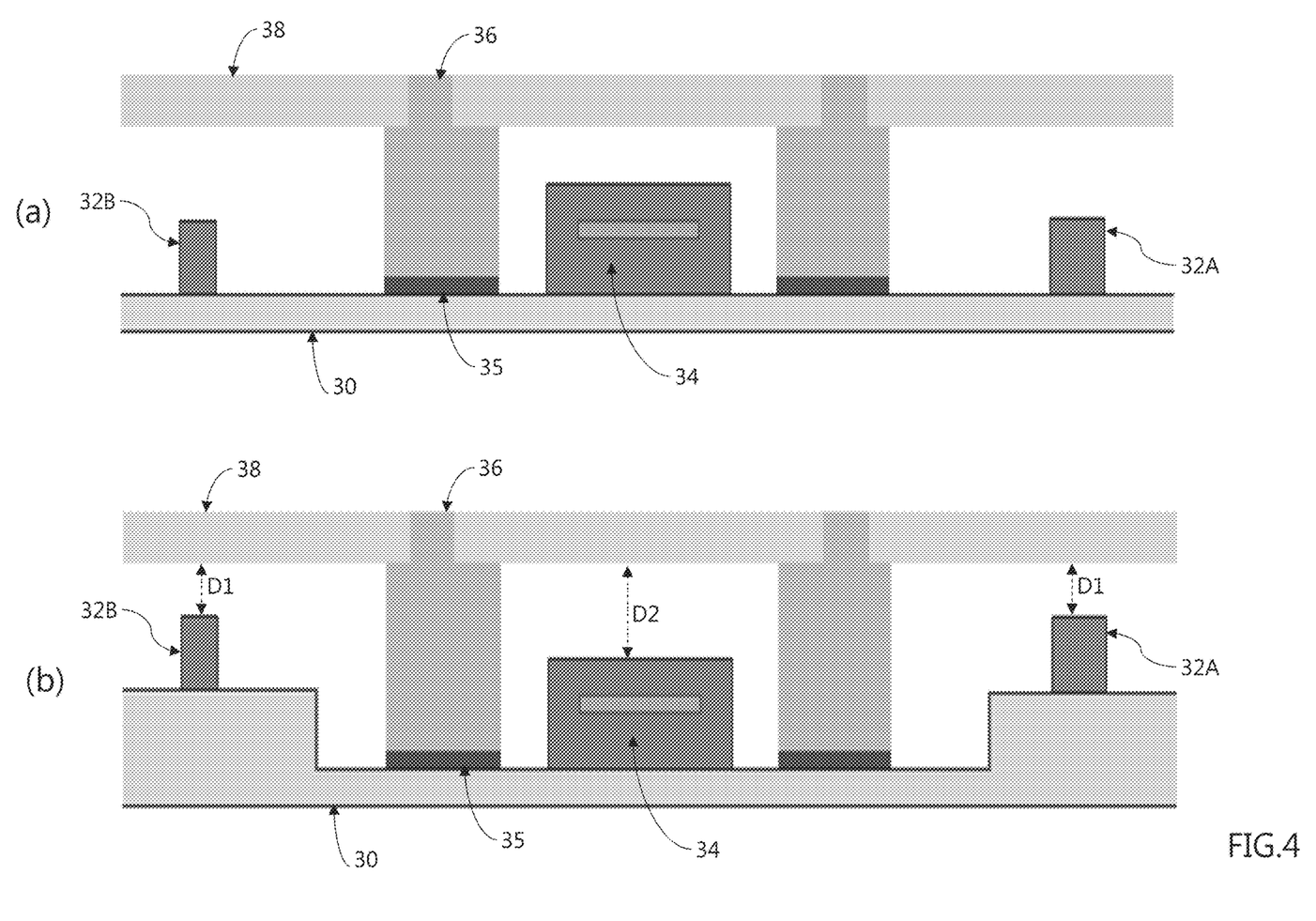
FIG. 4 shows a second structure of the apparatus for measuring a bio-signal according to embodiments of the present disclosure.

FIG. 4 shows a second structure of the apparatus for measuring a bio-signal according to embodiments of the present disclosure.

As shown in FIG. 4, the apparatus for measuring the bio-signal can include a light source 32A, 32B configured to emit a predetermined amount of light into a human body, a light receiving unit 34 configured to receive some of the predetermined amount of light, and a cover 38, which can be touched by the human body, configured to protect the light source 32A, 32B and the light receiving unit 34. The light source 32A, 32B and the light receiving unit 34 can be formed on a substrate (or a support layer 30). For the way of example but not limitation, the light source 32A, 32B can include a light-emitting diode (LED) emitting at least one of an infrared ray and a visible ray, while the light receiving unit 34 can include a photo diode detecting a light or a ray to generate an electric signal.

Referring to (a) of FIG. 4, the apparatus for measuring the bio-signal can further include a light barrier 36 formed between the light source 32A, 32B and the light receiving unit 36. In order to reduce noises entered with valid rays, it is preferable that all light or rays except for the valid rays which are emitted from the light source 32A, 32B and reflected or refracted by an inner part under a skin. Accordingly, it is necessary that the light receiving unit 36 is mechanically isolated from the other components of the apparatus. The light barrier 36 is a kind of shield (or multiple shields) which prevents a ray emitted from the light source 32A, 32B from entering into the light receiving unit 36 without passing through or being reflected or refracted by a human body. Particularly, the light barrier 36 can be extended into the cover 38 so as to isolate the light receiving unit 36 from the light source 32A, 32B. The light barrier 36 can be formed over the substrate or the support layer 30 via a bonding layer 35.

Further, in order that the light receiving unit 34 detects more rays or light as well as the light source 32A, 32B is not obstructed to emit a ray, an upper portion of the light barrier 36 can be narrower or smaller than a lower portion of the light barrier 36 isolating the light receiving unit 34 from the light source 32A, 32B.

Referring to (b) of FIG. 4, a first distance D1 between the light source 32A, 32B and the cover 38 is less than a second distance D2 between the light-emitting unit 34 and the cover 38. While the light source 32A, 32B and the light receiving unit 34 included in the apparatus shown in (a) of FIG. 4 are formed on the same flat surface, i.e., the substrate 30, it is advantageous to improve a quality of signals that the light source 32A, 32B is arranged closer to a skin as much as possible but the light receiving unit 36 is arranged away from the skin as far as possible. This is because, as the light source 32A, 32B is arranged closer to the skin, more light or rays can be delivered into a human body and noises including a surface reflection ray, e.g., a ray reflected by the skin, can be reduced. Meanwhile, as the light receiving unit 34 is closer to the skin, an amount of detectable rays is reduced since an optically receivable area is smaller.

By way of example but not limitation, when a wearable device for measuring a bio-signal is worn in a wrist, it is necessary to receive all of light or rays existing in as a larger area as possible since a vascularity at the wrist is not uniformed. However, if the wearable device is so far away from a skin, a signal strength can be very weak. Thus, it is required that the light source 32A, 32B and the light receiving unit 34 are located a proper distance away from the skin (or a human body).

Like a case shown in (b) of FIG. 4, in order that the first distance D1 between the light source 32A, 32B and the cover 38 is less than the second distance D2 between the light receiving unit 34 and the cover 38, some of the substrate or the support layer 30 where the light receiving unit 34 and another of the substrate or the support layer 30 where the light source 32A, 32B can have different heights. Adjusting a height of the substrate or the support layer 30 differently is just one of examples. Additional buffer layers or support layers (not shown) can be formed so as to make the first distance D1 smaller than the second distance D2.

Figure 5:
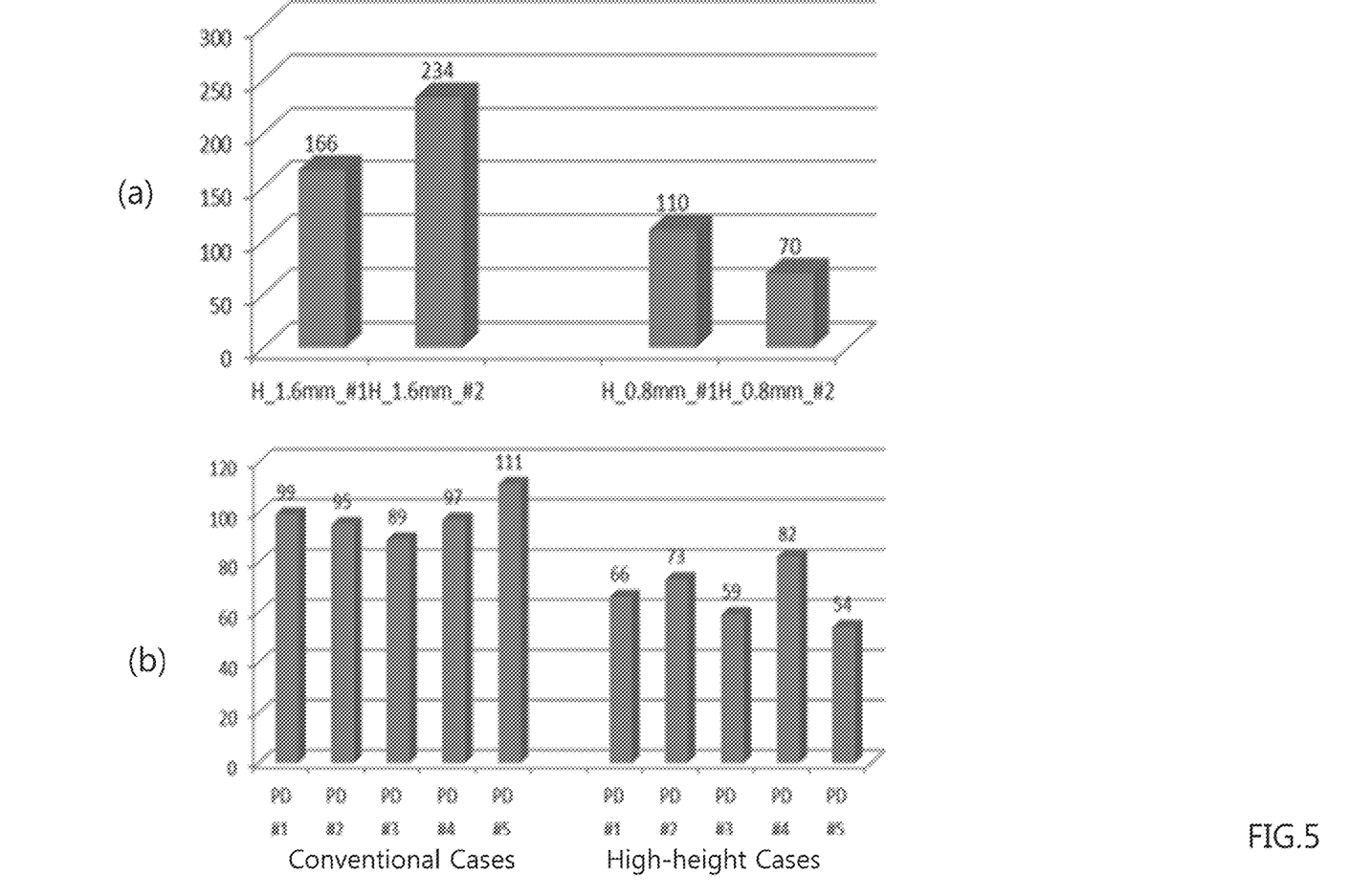
FIG. 5 describes an effect that can come from the second structure shown in FIG. 4.

FIG. 5 describes an effect that can come from the second structure shown in FIG. 4. Particularly, (a) shows a quality of signals based on different heights of the light source 32A, 32B shown in FIG. 4, while (b) shows a quality of signals based on different heights of the light receiving unit 34 shown in FIG. 4.

Referring to (a) of FIG. 5, a quality of signals in a case when a height of the light source is about 1.6 mm is better than one in another case when the height of the light source is about 0.8 mm.

Referring to (b) of FIG. 5, as a height of the light receiving unit is higher, a quality of signals can be improved averagely.

Accordingly, when the first distance between the light source and the cover is less than 1 mm while the second distance between the light receiving unit and the cover is larger than the first gap and less than 2 mm, a quality of signals of the apparatus for measuring the bio-signal can be enhanced.

Figure 6:
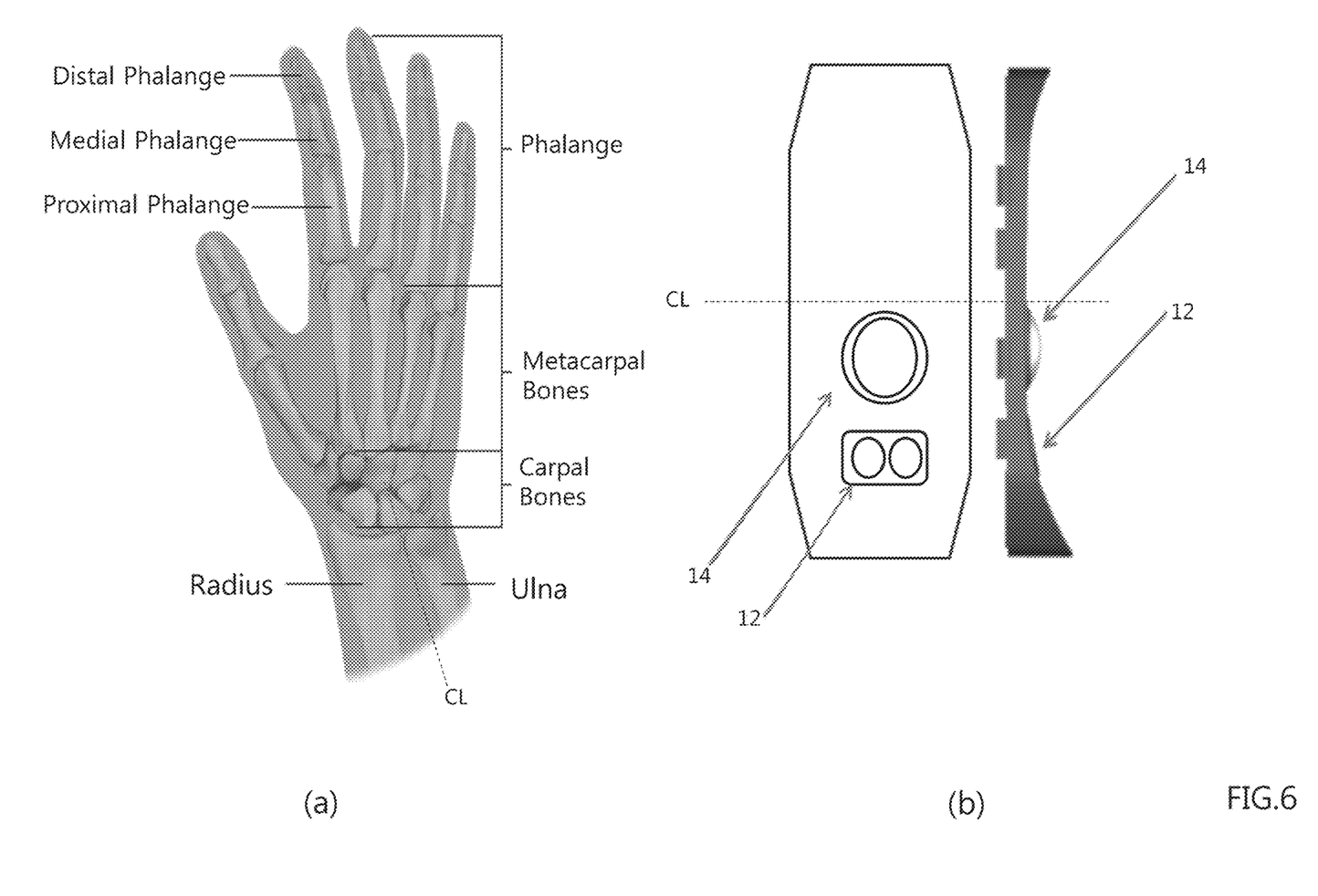
FIG. 6 shows a third structure of the apparatus for measuring a bio-signal according to embodiments of the present disclosure.

FIG. 6 shows a third structure of the apparatus for measuring a bio-signal according to embodiments of the present disclosure. Particularly, (a) shows a structure of human hand and wrist, while (b) shows an arrangement and a structure of the apparatus for measuring the bio-signal.

Because an internal structure in a human wrist rather than a human fingertip is very irregular or various, a quality of signals in the apparatus can be different based on a location difference of about 1 to 2 mm. Since the apparatus worn in the wrist to measure the bio-signal can generally handle a reflected ray not a penetrated ray, a quality of signals can be easily enhanced as an amount of rays reflected by a human body or tissue is larger.

Referring to (a) of FIG. 6, in the human wrist, there are two main bones: a radius and an ulna. Between them, the radius has a larger flat or area than the ulna, and the radius is generally located closer to a center CL in the wrist rather than the ulna. When the apparatus for measuring the bio-signal is designed to be worn in the wrist, the bone structure of human wrist can be considered. Because a lot of light or rays can be reflected by a bone and the radius has a larger area, more light or rays can be reflected at a part over the radius rather than the center CL of the human wrist. Thus, as optical sensors locates closer to the radius not in the middle of wrist, a quality of signals can be improved.

Referring to (b) of FIG. 6, the apparatus for measuring the bio-signal includes a light source 12 and a light receiving device 14. Both the light source 12 and the light receiving device 14 are arranged on one side from the center CL. In the apparatus for measuring the bio-signal based on reflected light or rays, a light receiving device should recognize or collect light or rays reflected by a human body (e.g., a bone, a blood vessel, a tissue, etc.). Accordingly, it can be desirable that the light source 12 and the light receiving device 14 arranged on one side from the center CL can be placed over the radius.

Unlike an apparatus including the light source 12 and the light receiving device 14 arranged in the center CL, in the apparatus including the light source 12 and the light receiving device 14 arranged on one side from the center CL, locations of the light source 12 and the light receiving device 14 can be different based upon whether the apparatus is left-handed or right-handed.

Figure 7:
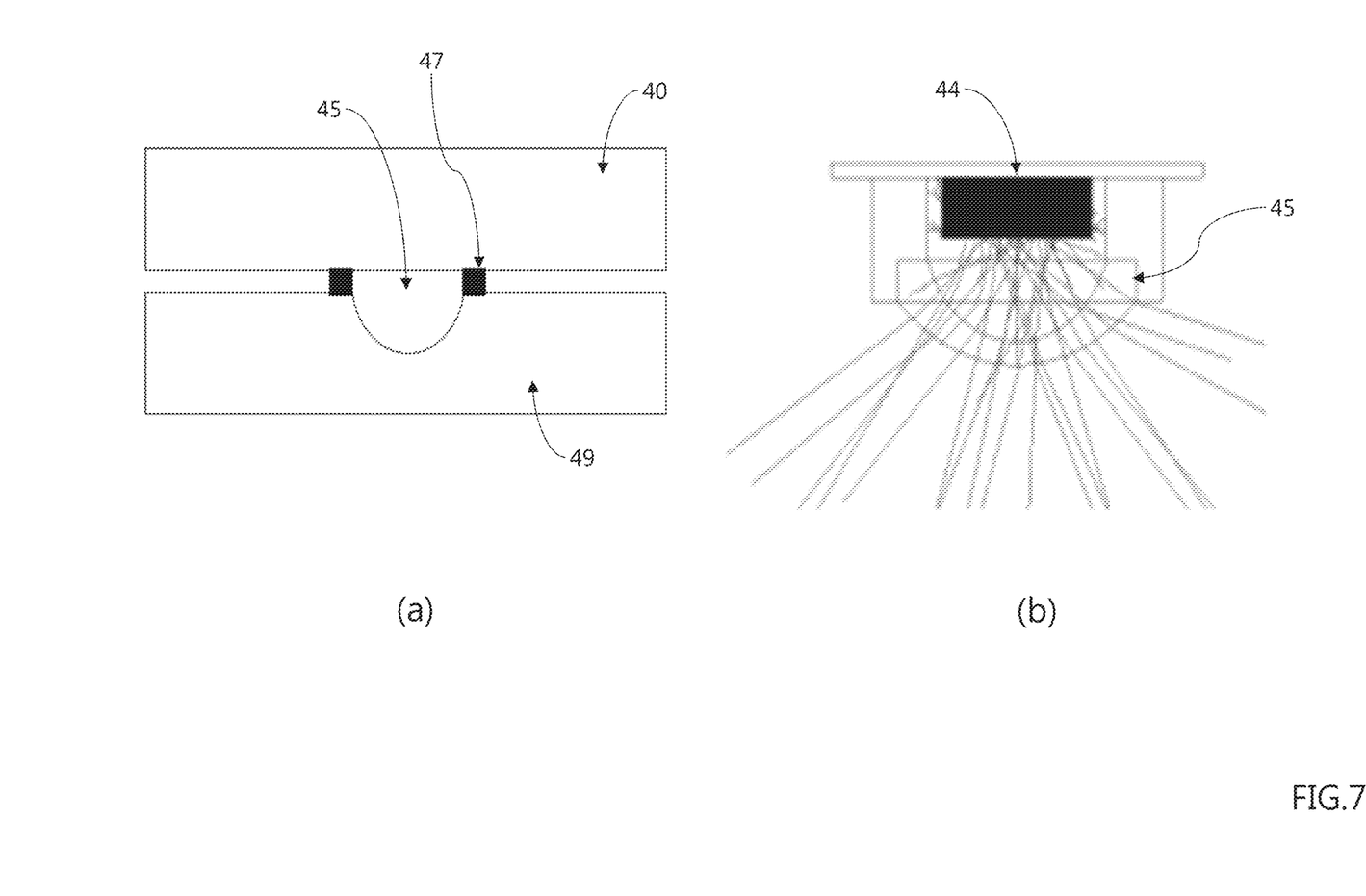
FIG. 7 shows a fourth structure of the apparatus for measuring a bio-signal according to embodiments of the present disclosure.

FIG. 7 shows a fourth structure of the apparatus for measuring the bio-signal according to embodiments of the present disclosure. Particularly, (a) describes a structure of a lens 45 formed over the light receiving device, and (b) describes functions and effects of the lens 45.

As shown in FIG. 7, a bio-signal measuring apparatus 40 can further include the lens 45 so as to enhance an efficiency of receiving or detecting a light or rays in a light receiving device 44. The lens 45 formed over the light receiving device 44 included in the bio-signal measuring apparatus 40 can be a sort of concave lens collecting or focusing a light or rays on the light receiving device 44 to improve a performance. However, an exterior surface of the lens 45 can be protruded like a convex lens so that some or all of the exterior surface can be stuck to, or covered by, a skin 49. By the way of example but not limitation, some of a cover over the light receiving device 44 can be formed in a convex shape. If the skin 49 covers the lens 45, lights or rays existing on the periphery of the bio-signal measuring apparatus 40, which is considered noise, can be blocked to enter into as well as an amount of light or rays entered from an inner part of human body inside the skin 49 can be increased so that a quality of signals is improved.

Further, the bio-signal measuring apparatus 40 can further include a blocking layer 47 surrounding some of lens 45 having a convex shape. The blocking layer 47 can effectively block light or rays existing on the periphery of the bio-signal measuring apparatus 40, which can be collected via the lens 45.

Figure 8:
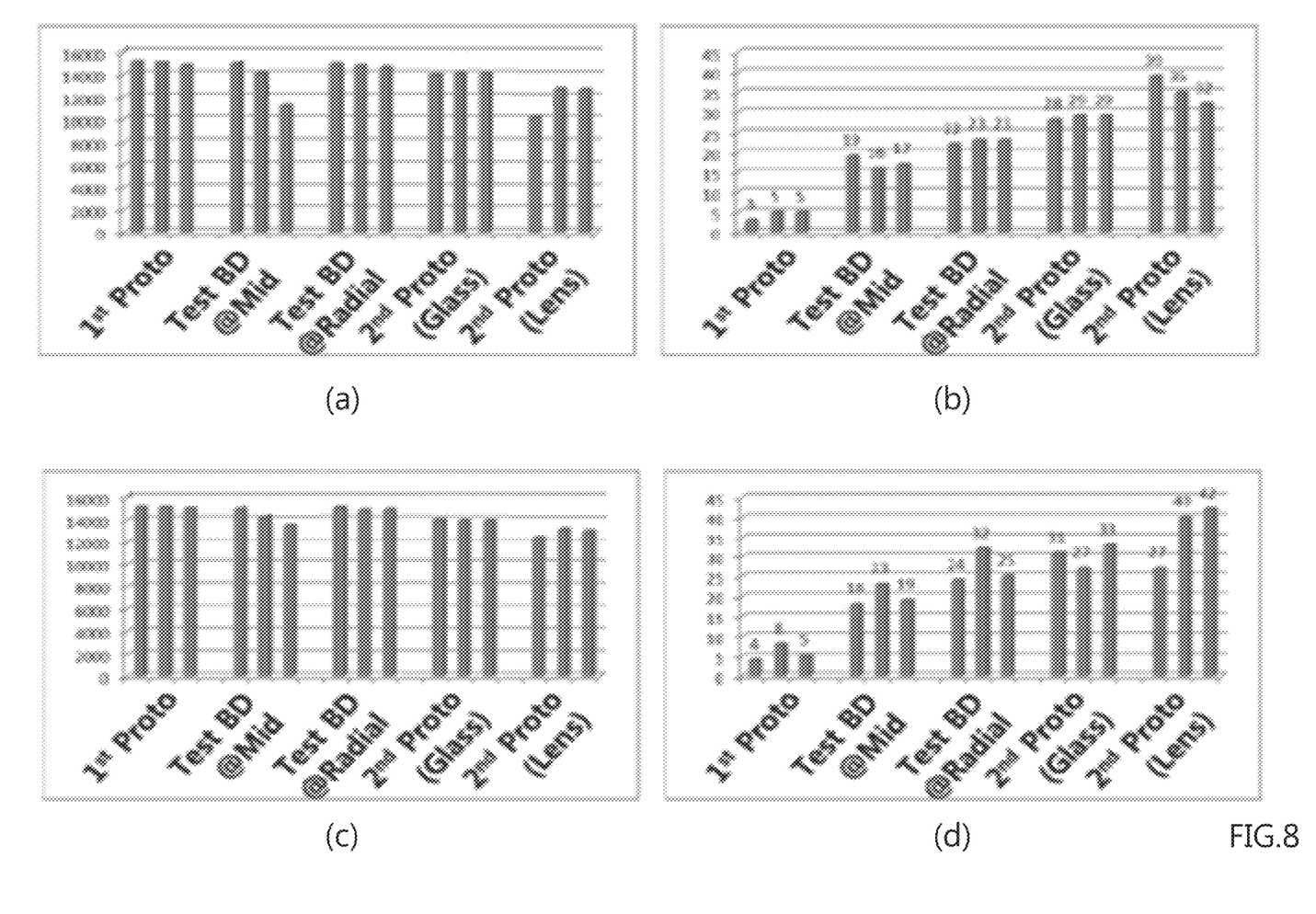
FIG. 8 shows an effect that can come from the third and fourth structures shown in FIGS. 6 and 7.

FIG. 8 shows an effect that can come from the third and fourth structures shown in FIGS. 6 and 7. Therein, (a) to (d) provide compared results regarding qualities of signals, each obtained by a basic prototype model ($1^{st}$ Proto), a middle model (Test BD@Mid) including both the light source and the light receiving device arranged on the center CL, a radial model (Test BD@Radial) including both the light source and the light receiving device arranged on one side from the center CL, a flat model ($2^{nd}$ Proto(Glass)) including a flat glass without a lens, and a lens model ($2^{nd}$ Proto(lens)) including a lens over the light receiving device.

Particularly, (a) of FIG. 8 shows a quality of signals based on a direct current (DC) component measured by a PPG sensor using an infrared ray, while (b) of FIG. 8 shows a quality of signals based on an alternating current (AC) component measured by the PPG sensor using the infrared ray. Further, (c) of FIG. 8 describes a quality of signals based on a direct current (DC) component measured by a PPG sensor using a red-colored ray, while (d) of FIG. 8 shows a quality of signals based on an alternating current (AC) component measured by the PPG sensor using the red-colored ray. Herein, a PPG signal measured by the PPG sensor can include an alternating current (AC) component used for monitoring a change of an amount of bloods synchronized with cardiac impulses (e.g., heartbeats) and a direct current (DC) component such as a low-frequency band signal, which is used for recognizing a bio-signal relevant to a respiration, a response of autonomic nervous system, and/or a regulation of body temperature.

Referring to (a) to (d) of FIG. 8, regardless of whether the PPG sensor uses the infrared ray or the red-colored ray, the radial model (Test BD@Radial) including both the light source and the light receiving device arranged on one side from the center CL has a better quality of signals based on the direct current (DC) component than the middle model (Test BD@Mid) including both the light source and the light receiving device arranged on the center CL. However, the lens model ($2^{nd}$ Proto(lens)) including a lens over the light receiving device has a litter worse quality of signals based on the direct current (DC) component than the flat model ($2^{nd}$ Proto(Glass)).

With regard to a quality of signals based on the alternating current (AC) component, regardless of whether the PPG sensor uses the infrared ray or the red-colored ray, the radial model (Test BD@Radial) including both the light source and the light receiving device arranged on one side from the center CL has a better performance than the middle model (Test BD@Mid) including both the light source and the light receiving device arranged on the center CL. Further, the lens model ($2^{nd}$ Proto(lens)) including a lens over the light receiving device has a better performance than the flat model ($2^{nd}$ Proto(Glass)).

By way of example but not limitation, if the above-described arrangement and/or structure is applied to a PPG sensor for monitoring the change of the amount of bloods synchronized with cardiac impulses, a quality of bio-signals obtained at a wrist can be improved 7 to 10 times beyond a conventional wrist wearable device (e.g., as shown in FIG. 1). When using improved bio-signals, an bio-signal measuring apparatus can recognize or extract information regarding an oxygen saturation in a blood, which cannot be measured or recognized due to a low quality of signals.

As described above, a quality of signal regarding a PPG signal can be improved about 7 to 10 times by a structure and an arrangement of both light-emitting and receiving devices included in a PPG sensor.

In addition, a bio-signal measuring apparatus as described above can have a structure and design suitable for facilitating an accurate measurement of a bio-signal in a human body.

The aforementioned embodiments are achieved by combination of structural elements and features of the disclosure in a predetermined manner. Each of the structural elements or features should be considered selectively unless specified separately. Each of the structural elements or features may be carried out without being combined with other structural elements or features. Also, some structural elements and/or features may be combined with one another to constitute the embodiments of the disclosure. The order of operations described in the embodiments of the disclosure may be changed. Some structural elements or features of one embodiment may be included in other embodiments, or may be replaced with corresponding structural elements or features of other embodiments.

It will be apparent to those skilled in the art that various modifications and variations can be made in the disclosure without departing from the spirit or scope of the disclosure. Thus, it is intended that the disclosure covers the modifications and variations of this disclosure provided they come within the scope of the appended claims and their equivalents.

What is claimed is:

1. An apparatus for measuring a bio-signal, comprising:
a light source configured for emitting a predetermined amount of light into a human body;
a light receiving unit receiving at least some of the predetermined amount of light;
a light barrier formed between the light source and the light receiving unit; and
a cover, which is touchable by the human body, protecting the light source and the light receiving unit,
wherein the light source and the cover are arranged such that the light source and the cover are separated by a first gap,
wherein the light receiving unit and the cover are arranged such that the light receiving unit and the cover are separated by a second gap,
wherein the first gap is less than the second gap,
wherein an upper portion of the light barrier extending into the cover is narrower than a lower portion of the light barrier isolating the light receiving unit from the light source,
wherein the light source is formed on a first support layer having a first height, and
wherein the light receiving unit and the light barrier are formed on a second support layer having a second height lower than the first height of the first support layer.

2. The apparatus according to claim 1, wherein the light source and the light receiving unit are arranged with a separation distance between them of 5 to 6 mm.

3. The apparatus according to claim 2, wherein the light source emits at least one of an infrared ray and a visible ray.

4. The apparatus according to claim 2, wherein:
an amount of light is reflected by a portion of the human body and enters into the light receiving unit,
the portion of the human body is a wrist, and
both of the light source and the light receiving unit are configured to be located over a radial in the wrist.

5. The apparatus according to claim 1, wherein the first gap between the light source and the cover is less than 1 mm, while the second gap between the light receiving unit and the cover is less than 2 mm.

6. The apparatus according to claim 1, wherein the light barrier extends into the cover so that a portion of the cover covering the light source is separate from a portion of the covering over the light receiving unit.

7. The apparatus according to claim 1, further comprising a lens disposed over the light receiving unit.

8. The apparatus according to claim 7, wherein the lens is a concave lens having a convex surface.

9. The apparatus according to claim 1, wherein the apparatus detects a photoplethysmography (PPG) signal based on a change of an amount of light received at the light receiving unit.

10. An photoplethysmography (PPG) sensor, comprising:
a light-emitting diode and a photo diode formed over a first support layer and a second support layer, respectively;
an isolating barrier formed between the light-emitting diode and the photo diode; and
a cover protecting the light-emitting diode and the photo diode,
wherein the light-emitting diode and the cover are arranged such that the light-emitting diode and the cover are separated by a first gap,
wherein the photo diode and the cover are arranged such that the photo diode and the cover are separated by a second gap,
wherein the first gap is less than the second gap, wherein an upper portion of the isolating barrier extending into the cover is narrower than a lower portion of the isolating barrier isolating the photo diode from the light-emitting diode, wherein the light-emitting diode is formed on the first support layer having a first height, and wherein the photo diode and the isolating barrier are formed on the second support layer having a second height lower than the first height of the first support layer.

11. The PPG sensor according to claim 10, wherein the light-emitting diode emits at least one of an infrared ray and a visible ray.

12. The PPG sensor according to claim 10, wherein the light-emitting diode and the photo diode are arranged with a separation distance between them of 5 to 6 mm.

13. The PPG sensor according to claim 10, wherein the light-emitting diode includes a plurality of light-emitting diodes, each located adjacent to one another.

14. The PPG sensor according to claim 10, wherein locations of the light-emitting diode and the photo diode differ according to a part of a human body on which the PPG sensor is worn.

15. The PPG sensor according to claim 10, wherein both of the light-emitting diode and the photo diode are configured to be located over a radial in a wrist.

16. The PPG sensor according to claim 10, wherein the first gap is less than 1 mm, while the second gap is less than 2 mm.

17. The PPG sensor according to claim 10, wherein the isolating barrier extends into the cover so that a portion of the cover covering the light-emitting diode is separate from a portion of the cover covering the photo diode.

18. The PPG sensor according to claim 10, further comprising a blocking layer surrounding a portion of the cover positioned over the photo diode, the portion of the cover being formed in a convex shape.

* * * * *